United States Patent [19]

Meijer et al.

[11] Patent Number: 5,190,725
[45] Date of Patent: Mar. 2, 1993

[54] CHEMICAL TREATMENT OF AN INFECTIOUS WASTE

[75] Inventors: Robert S. Meijer, San Diego; John P. Frain, Oceanside, both of Calif.

[73] Assignee: Winfield Industries, San Diego, Calif.

[21] Appl. No.: 692,195

[22] Filed: Apr. 26, 1991

Related U.S. Application Data

[63] Continuation-in-part of Ser. No. 510,700, Apr. 19, 1990, abandoned.

[51] Int. Cl.$^5$ .............................................. A01N 59/00
[52] U.S. Cl. ....................................... 422/37; 423/477; 423/DIG. 18; 588/205; 241/17; 241/22; 241/DIG. 38
[58] Field of Search ................... 422/37; 424/661, 665; 423/477, DIG. 18, DIG. 20; 206/524.3, 524.4; 588/205; 241/17, 22, DIG. 38, 606

[56] References Cited

U.S. PATENT DOCUMENTS

| | | | |
|---|---|---|---|
| 2,791,324 | 5/1957 | Knoop et al. | 206/47 |
| 3,279,511 | 10/1966 | Griffin | 150/1 |
| 4,084,747 | 4/1978 | Alliger | 423/477 |
| 4,256,256 | 3/1981 | Meyers | 229/56 |
| 4,504,442 | 3/1985 | Rosenblatt et al. | 422/37 |
| 4,533,691 | 8/1985 | Khalil et al. | 524/401 |
| 4,578,185 | 3/1986 | Wilson et al. | 210/85 |
| 4,614,267 | 9/1986 | Larkin | 206/221 |
| 4,671,882 | 6/1987 | Douglas et al. | 210/720 |
| 4,731,193 | 3/1988 | Mason et al. | 422/37 |
| 4,776,455 | 10/1988 | Anderson et al. | 206/0.5 |
| 4,809,915 | 3/1989 | Koffsky et al. | 241/36 |
| 4,861,514 | 8/1989 | Hutchings | 423/477 |
| 4,889,654 | 12/1989 | Mason et al. | 422/37 |
| 4,917,238 | 4/1990 | Schumacher | 206/223 |
| 4,925,645 | 5/1990 | Mason | 423/477 |
| 4,945,992 | 8/1990 | Sacco | 422/37 |

FOREIGN PATENT DOCUMENTS 0959238 12/1974 Canada ............................ 423/477
0037355 2/1989 Japan .

OTHER PUBLICATIONS

Block, Seymour S., *Disinfection, Sterilization, and Preservation*, 1983, pp. 755–759, 797, and 822–825, 542–544.
Whitten, Kenneth W. and Gailey, Kenneth D., *General Chemistry*, 2nd Ed., "Chemical Kinetics", (1984) pp. 478–490.

*Primary Examiner*—Robert J. Warden
*Assistant Examiner*—Laura E. Collins
*Attorney, Agent, or Firm*—Nydegger & Associates

[57] ABSTRACT

An infectious waste, a solid chlorite salt, a solid acid and a preheated aqueous solvent are mixed in a treatment volume. At least a portion of the chlorite salt and acid is dissolved in the preheated aqueous solvent incident to mixing and is reacted to form a treatment solution containing a chlorine dioxide disinfectant and a byproduct acid salt. The infectious waste is contacted with the chlorine dioxide in the treatment solution which attacks and destroys the infectious constituents of the waste, thereby decontaminating the waste. Upon dewatering, the decontaminated waste is suitable for landfilling. Process control is exercised by controlling the temperature of the aqueous solvent. A solvent temperature is selected which optimizes both the chlorine dioxide concentration in the treatment solution and the reactivity of the chlorine dioxide with the infectious constituents. Continuous monitoring of the chlorine dioxide concentration in the treatment solution enables adjustment of the solvent preheat temperature to optimal values in accordance with the dynamics of the treatment system.

14 Claims, 1 Drawing Sheet

CHEMICAL TREATMENT OF AN INFECTIOUS WASTE

This application is a continuation-in-part application of my prior co-pending patent application for a "Bag with Disinfectant for Sterilizing Infectious Waste" Ser. No. 510,700 filed Apr. 19, 1990, now abandoned.

FIELD OF THE INVENTION

The present invention relates generally to methods for treating infectious waste. More particularly, the present invention relates to methods which chemically decontaminate infectious waste prior to disposal. The present invention is particularly, though not exclusively, useful for decontaminating infectious waste with a disinfectant in solution which is formulated from dry particulate precursors.

BACKGROUND OF THE INVENTION

The disposal of infectious waste from hospitals and other medical establishments is a major problem. Indeed, the importance of proper and effective infectious waste disposal has become of greater concern in recent years, due to an increased awareness of health problems such as the AIDS epidemic. In part because of the AIDS epidemic, definitions of what constitutes "infectious waste" are being broadened. Consequently, the volume of infectious waste which must be disposed of is increasing. Accordingly, the need for a system or apparatus which will accomplish the safe, efficacious, and cost effective disposal of significant volumes of infectious waste is growing. The need is particularly great for the disposal of solid infectious waste. Solid medical wastes consist primarily of plastic, paper, fabric, glass, and metal which are embodied in such articles as syringes, bottles, tubes, dressing and the like. In the past, these wastes were simply landfilled, but now government regulation generally requires decontamination before disposal.

One method for decontaminating and disposing of infectious waste involves incineration, wherein the waste is burned and the decontaminated ashes are properly disposed. An alternative waste disposal method is to disinfect the waste in a steam autoclave or ethylene oxide autoclave prior to waste disposal. While effective for their intended purposes, both incinerators and autoclaves present ancillary waste disposal problems. Incinerators, for example, are difficult and costly to construct and are relatively expensive to maintain in an environmentally safe manner. Autoclaves too, present additional problems, such as odor, cost and operational complexity. Additionally, waste which has been disinfected by autoclaving typically requires further disposal procedures, such as incineration, prior to final disposition of the waste in such places as ordinary landfills.

With the above discussion in mind, alternative infectious waste disposal systems have been proposed to disinfect the waste. According to these proposals, the waste is contacted with a disinfectant solution containing a chlorine compound to decontaminate the waste. The decontaminated solid may then be disposed in ordinary landfills.

Unfortunately, decontamination of waste using chlorine compounds presents certain technical complications. First, liquid disinfectant loses its disinfectant potency during prolonged storage. Thus, there is a need to use liquid disinfectant that is relatively "fresh" in order to achieve an acceptable degree of waste decontamination. Second, it is relatively difficult to ensure that an appropriate concentration of the disinfectant has been contacted with the waste during the treatment process to sufficiently decontaminate the waste. It is also important, however, to avoid applying too high a concentration of chlorine compound to the waste in order to avoid certain undesirable results, such as corrosive effects and the release of toxic gasses. The present invention recognizes that dry solid precursors of a chlorine based disinfectant can be stored for a relatively lengthy period of time without losing their potency and can ultimately be mixed with water to form the chlorine based disinfectant which is used to decontaminate infectious waste.

Accordingly, it is an object of the present invention to provide a method for infectious waste treatment in which dry solid disinfectant precursors are mixed with the infectious waste and wetted to produce a decontaminated waste suitable for landfilling. Another object of the present invention is to provide a method for infectious waste treatment wherein process control can be effected with relative ease. Yet another object of the present invention is to remove excess treatment solution from the treated waste before landfilling. Finally, it is an object of the present invention to provide a method for infectious waste treatment which is comparatively cost-effective from a capital and operational standpoint.

SUMMARY OF THE INVENTION

The present invention is a method for treating an infectious waste comprising preliminarily storing the waste and a pair of dry solid disinfectant precursors in isolated compartments of a disposal container. One precursor is a particulate chlorite salt and the other is a particulate acid. Treatment is initiated by mechanically destroying the disposal container to mix the solids contained therein, while simultaneously wetting the solids mixture with a temperature-controlled aqueous solvent. Incident to mixing and wetting of the solids, the infectious waste is mechanically fragmented into smaller particle sizes and at least a portion of each disinfectant precursor is dissolved in the solvent.

The chlorite salt and acid are subsequently reacted in solution at the solvent preheat temperature to form a disinfectant, i.e., chlorine dioxide, and a byproduct acid salt. The infectious waste is contacted with the chlorine dioxide-containing treatment solution which attacks and destroys the infectious constituents of the waste, thereby decontaminating the waste. Upon dewatering, the decontaminated waste is suitable for ordinary landfilling.

Process control of the present treatment method is exercised primarily by regulating the temperature of the aqueous solvent. Since the objective is to destroy the infectious constituents of the waste, a solvent temperature is selected which optimizes both the chlorine dioxide concentration in the treatment solution and the reactivity of the chlorine dioxide with the infectious constituents. Continuous monitoring of the chlorine dioxide concentration in the treatment solution enables adjustment of the solvent temperature to optimal values in accordance with the dynamics of the treatment system.

Maintenance of a sufficient chlorine dioxide concentration in the treatment solution is further enabled by initiating the treatment with quantities of solid chlorite salt and acid in stoichiometric excess of quantities required to achieve a minimum acceptable degree of decontamination. Consequently, adequate levels of chlorine dioxide can be maintained in the treatment solution even as the chlorine dioxide is being consumed in reaction with the organic and infectious infectious constituents of the waste or is escaping as a gas from the treatment solution.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENT

The present invention generally comprises formulating a disinfectant solution from an aqueous solvent and dry particulate disinfectant precursors, contacting an infectious waste with the resulting disinfectant solution, and decontaminating the infectious waste with the disinfectant dissolved therein. The terms "disinfect" and "decontaminate" are used synonymously herein and refer to the destruction of a substantial portion of infectious constituents within the infectious waste sufficient to render the waste substantially noninfectious.

A preferred means of formulating the solution and contacting the waste with the solution is described below with reference to the drawings. It is, however, understood that the present invention is not limited to this particular preferred means of performing the above-described steps. Other means known to one skilled in the art which enable formulation of the disinfectant solution from a solvent and dry precursors and contacting the waste with the resulting disinfectant may be employed within the scope of the present invention.

Figure 1:
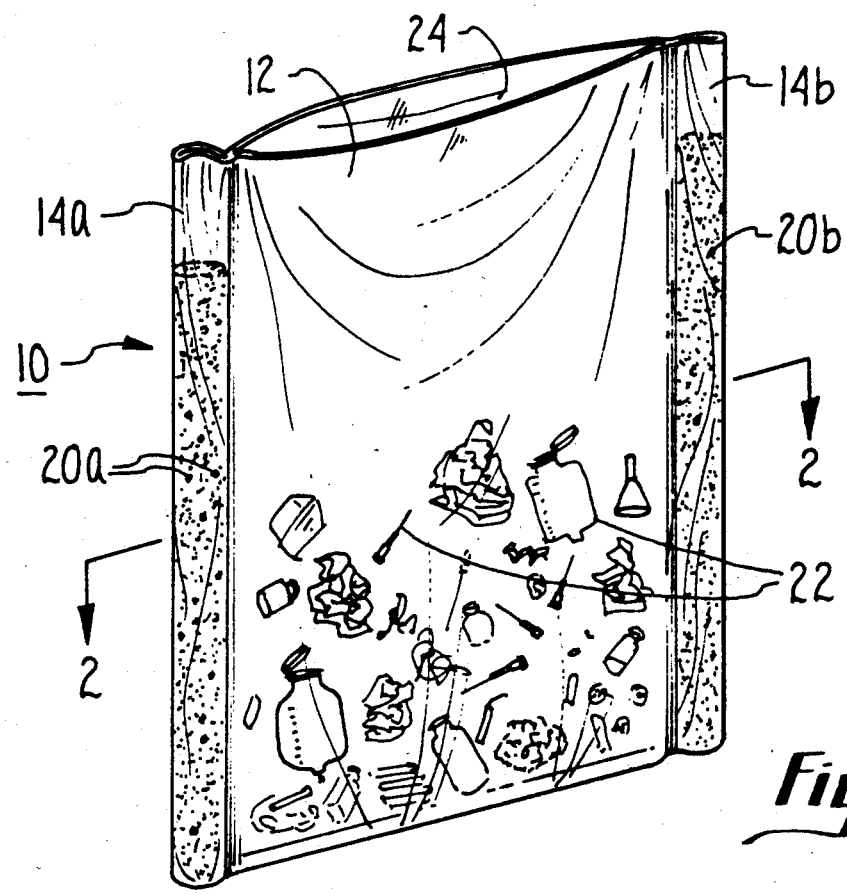
FIG. 1 is an isometric view of a disposal container having utility in the present invention.

A disposal container generally designated 10 is shown in FIG. 1. Container 10 comprises waste compartment 12 and disinfectant precursor compartments 14a and 14b. Container 10 is preferably a bag made of a lightweight, flexible, yet strong material, such as a plastic material or any of the well-known nonporous materials which are widely used in the fabrication of bags.

Figure 2:
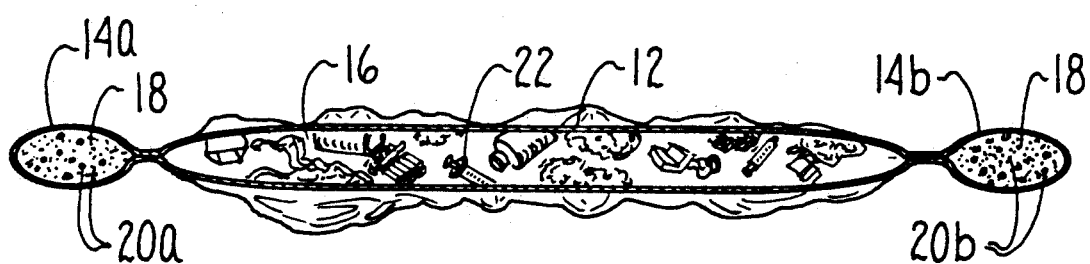
FIG. 2 is a cross-sectional view of the disposal container having utility in the present invention as seen along the line 2—2 in FIG. 1.

Referring additionally to FIG. 2, waste compartment 12 forms a void 16, and precursor compartments 14a and 14b form cavities 18a, 18b, respectively. Disinfectant precursors 20a, 20b, are held in each of the fully enclosed and presealed cavities 18a and 18b such that precursors 20a, 20b are maintained separate from one another and from void 16 containing infectious waste 22 until the present treatment method is initiated. Infectious waste 22 is placed into void 16 of waste compartment 12 through open end 24. The subsequent passage of infectious waste 22 out of waste compartment 12 through end 24 is prevented by appropriately closing and sealing end 24.

When it is desired to initiate the treatment method of the present invention, sealed waste-filled container 10 is placed in a treatment volume (not shown) which is preferably an enclosed reaction vessel. Container 10 is mechanically destroyed in the treatment volume by shredding, pulverizing, or the like. The destruction of container 10, includes the destruction of compartments 12, 14a, 14b, thereby releasing the disinfectant precursors 20a, 20b from compartments 14a, 14b onto the infectious waste from compartment 12. Concomitant with the destruction of container 10 and mixing of precursors 20a, 20b with the infectious waste 22 is the mechanical breaking up of the infectious waste 22 into particle sizes smaller than those initially placed in void 16. A preferred particle size of the waste 22 which facilitates its mixing with precursors 20a, 20b and contacting with the disinfectant is between about 0.4 and 1.5 cm, and most preferably about 0.5 and 1 cm.

During breaking up and mixing of the waste with the disinfectant precursors, a preheated aqueous solvent is injected into the treatment volume. Injection of the solvent preferably comprises spraying the solvent from a plurality of jets in the treatment volume onto the contents thereof to achieve adequate mixing of the solvent and solids. The resulting composition is a well-mixed hot mash of infectious waste, disinfectant precursors and aqueous solvent. The mash presents an ideal environment for decontamination of the waste. The present treatment method is described below in terms of the specific compositions of the disinfectant precursors, disinfectant, and solvent and in terms of the process parameters relating thereto.

The pair of disinfectant precursors of the present invention are both initially in a solid state and preferably in a dry particulate state such as in a granular or powdered state. One precursor is a chlorite salt and preferably sodium chlorite. The other precursor is an acid, preferably a carboxylic acid, and most preferably a tricarboxylic acid, such as citric acid. Additional constituents may also be mixed with one or both of the precursors. For example, the precursors may contain a pigment constituent which, when mixed with liquid, forms a dye for staining the waste. Additionally, one or both of the precursors may contain a deodorant constituent, defoaming constituents or a surfactant. Surfactants, when mixed with the aqueous solvent during the present method, prevent the solvent from beading. It is desirable that the solution does not bead to ensure thorough mixing of the disinfectant solution with the waste. Lastly, the precursors may contain an inert filler material, such as sodium carbonate.

The aqueous solvent may be any aqueous liquid and is preferably an inert aqueous liquid such as water. Ordinary tap water is generally suitable for use in the present method. The aqueous solvent is within a temperature range of 5 to 70° C., preferably 10° to 60° C., and most preferably greater than about 20° C. upon mixing. Temperatures above ambient are preferably achieved by preheating the solvent by any conventional means prior to injection into the treatment volume.

Upon mixing of the disinfectant precursors with the aqueous solvent, at least a portion of the precursors are dissolved in the solvent and the dissolved precursor species are reacted in solution with one another to form chlorine dioxide and a salt of the acid. Thus, for example, where citric acid is the acid precursor and sodium chlorite is the chlorite salt precursor, the resulting products are substantially chlorine dioxide and sodium citrate. The chlorine dioxide is the active disinfectant product of this precursor reaction and the acid salt, sodium citrate, is essentially an inert byproduct.

The resulting solution is sufficiently mixed with the infectious waste to enable intimate contacting between the dissolved chlorine dioxide disinfectant and the infectious constituents of the waste. Chlorine dioxide is a strong oxidizing agent and biocide which within a relatively short time attacks and destroys infectious microorganisms residing in the waste, thereby decontaminating the waste.

The decontamination level, i.e., level of kill, attainable with the present method is a function of several interrelated parameters including disinfectant concentration, rate of disinfectant formation, treatment solution temperature, disinfectant solubility, and precursor solubility. Nevertheless, as is shown below, it has been found that the decontamination process can be satisfactorily operated simply as a function of two key parameters, disinfectant concentration and temperature.

Accordingly process control can be effected by selecting a desired level of kill, i.e., target kill, and adjusting the disinfectant concentration and treatment solution temperature to meet the preselected target kill. For example, a target kill of 6 decades ($10^6$ organisms/ml) is achieved within about five minutes or less for a typical infectious medical waste using a chlorine dioxide solution at a concentration of 30 ppm and a temperature of 50° C. In practice, however, the process is controlled by adjusting only temperature while monitoring variations in the disinfectant concentration as a baseline for temperature adjustment. Temperature is selected as the independent variable and disinfectant concentration as the dependant variable for the practical reason that the ability to independently adjust disinfectant concentration is somewhat limited when a fixed amount of precursor employed.

Process control is facilitated by recognition of the functional relationship between solution temperature and concentration of the disinfectant, chlorine dioxide, at a given level of kill n which is represented by the equation:

$$[ClO_2] = a_n e^{-k_n T} \quad (1)$$

wherein

[$ClO_2$] = chlorine dioxide concentration,

T = Temperature, and $a_n$, $k_n$ = empirically determined constants for $kill_n$.

Figure 3:
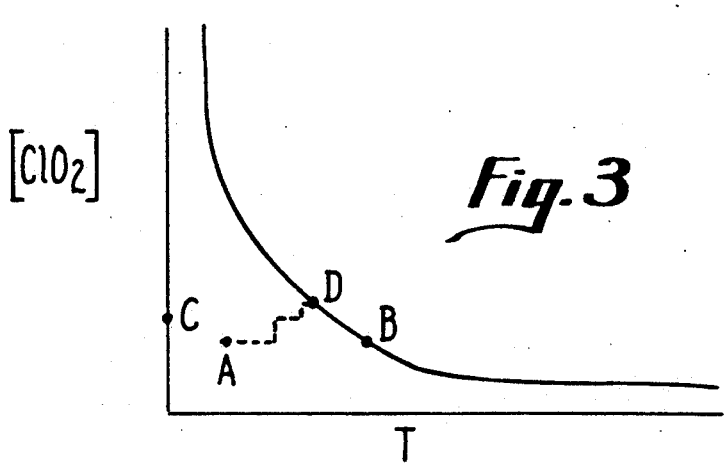
FIG. 3 is a generalized curve of the functional relation between treatment solution temperature and disinfectant concentration.

FIG. 3 generally depicts the shape of the curve for equation (1). Each point on the curve defines values of [$ClO_2$] and T at which $kill_n$ can be achieved. Accordingly, process control is more specifically implemented by preselecting the target kill, modeling the relationship between [$ClO_2$] and T at the target kill to define a curve, and adjusting the actual values of [$ClO_2$] and T to lie on the target kill curve.

FIG. 3 shows a typical start-up scenario for the present invention. The treatment solution is initially at point A which is inside the required curve for the target kill. Since it is desirable to operate on the curve, process control consequently raises the temperature of the solution toward point B which corresponds to the same chlorine dioxide concentration as point A, but at a higher temperature. Raising the temperature of the solution, however, increases the rate of chlorine dioxide formation, thereby increasing the chlorine dioxide concentration of the solution to a value designated by C on the vertical axis. Thus, as point B is approached, the required temperature on the curve falls. The dashed line shows this iterative equilibration procedure whereby an operating point designated by D is ultimately attained. Operation is preferably maintained on or above the curve on which point D lies.

Chlorine dioxide concentration is continuously monitored to determine whether the requirements of the treatment solution change. For example, if a relatively "dirty" waste is fed to the solution, the amount of $ClO_2$ consumed increases, reducing the $ClO_2$ concentration in the solution. Accordingly, the temperature of the solution must be iteratively increased in the manner ercited above to return operation to the curve. If a relatively "clean" waste is fed to the solution, the $ClO_2$ concentration increases, correspondingly reducing the temperature requirement. It is preferable to preselect a target kill exceeding a minimum acceptable level of kill so that adequate decontamination of the waste is achieved even when operation falls somewhat below the curve. It has generally been found that within the presently prescribed temperature range a minimum $ClO_2$ concentration in the treatment solution to achieve an acceptable level of kill is about 10 ppm up to the required concentration and preferably about 12 ppm up to the required concentration.

As noted above, starting quantities of the solid chlorite salt and acid are fixed according to the preferred embodiment. As such, they are preferably provided in stoichiometric excess of quantities necessary to produce the required chlorine dioxide concentrations shown on the curve of FIG. 3. Thus, adequate concentrations of dissolved precursors will be available in solution for chlorine dioxide production despite the fact that, in most cases, some of the solid precursors do not react, and the additional fact that a significant fraction of the chlorine dioxide is consumed by reaction with the infectious waste constituents or diffuses out of solution. By way of example, a typical relative starting concentration of precursors, solvent and waste which will provide a desired chlorine dioxide concentration, is on the order of 4.6 g/l sodium chlorite/3.3 g/l citric acid/12 kg of solid waste.

When the disinfectant reaction with the waste is completed, the product is a decontaminated wetted waste. The bulk of the precursors are consumed by reaction leaving, in addition to the solid waste, aqueous solvent, and acid salts, only residual trace amounts of precursors and chlorinated organics. The decontaminated waste is innocuous and suitable for ordinary landfilling. In preparation for landfilling, the waste may be dewatered to reduce its mass and the liquid recovered from dewatering may be reheated and recycled to the treatment volume as solvent.

While certain preferred conditions, quantities and other parameters were detailed in the above description of preferred embodiments, those can be varied, where suitable, with similar results. Various applications, variations and ramifications of this invention will occur to those skilled in the art upon reading the present disclosure. Those are intended to be included within the scope of this invention as defined in the appended claims.

I claim:

1. A method for treating an infectious waste comprising:

collecting infectious waste in a container having separate compartments containing a predetermined quantity of a chlorite salt and a predetermined quantity of an acid;

selecting a target kill level for said infectious waste in a treatment solution, said target kill level defined by a curve having the equation:

$$[ClO_2] = a_n e^{-knT},$$

wherein
- $n$ = said selected target kill level,
- $[ClO_2]$ = chlorine dioxide concentration of said treatment solution,
- $T$ = temperature of said treatment solution, and
- $a$, $k$ = empirically determined constants for a given kill level;

preheating an aqueous solvent to a preheat temperature in an auxiliary container;

mechanically breaking the container and infectious waste therein said auxiliary container into a smaller particle size for releasing and mixing said predetermined quantity of chlorite salt and said predetermined quantity of an acid with infectious waste particles in preheated aqueous solvent;

reacting said predetermined quantity of said chlorite salt and said predetermined quantity of said acid in said preheated aqueous solvent to generate said treatment solution comprising chlorine dioxide;

measuring an initial temperature and an initial chlorine dioxide concentration of said treatment solution;

comparing said initial temperature and said initial chlorine dioxide concentration to said curve;

adjusting the temperature of said treatment solution until said treatment solution achieves a temperature and a chlorine dioxide concentration on or above said curve to substantially disinfect said waste.

2. The method for treating an infectious waste as recited in claim 1 wherein said preheat temperature is greater than about 20° C.

3. The method for treating an infectious waste as recited in claim 1 wherein said chlorite salt is sodium chlorite.

4. The method for treating an infectious waste as recited in claim 1 wherein said acid is a carboxylic acid.

5. The method for treating an infectious waste as recited in claim 1 wherein said acid is citric acid.

6. The method for treating an infectious waste as recited in claim 1 wherein said acid and said chlorite salt are in a dry particulate state upon initiation of mixing.

7. The method for treating an infectious waste as recited in claim 1 wherein said treatment solution further comprises a salt of a carboxylic acid.

8. The method for treating an infectious waste as recited in claim 1 wherein said aqueous solvent is water.

9. The method for treating an infectious waste as recited in claim 1 wherein said aqueous solvent contains a surfactant.

10. The method for treating an infectious waste as recited in claim 1 wherein the temperature of said treatment solution is adjusted by adjusting said preheat temperature of said aqueous solvent.

11. The method for treating an infectious waste as recited in claim 1 wherein the mechanically breaking and reacting steps are performed substantially simultaneously.

12. A method for treating an infectious waste comprising:

collecting infectious waste in a container having separate compartments containing a predetermined quantity of solid sodium chlorite salt and a predetermined quantity of solid citric acid;

selecting a target kill level for said infectious waste in a treatment solution, said target kill level defined by a curve having the equation:

$$[ClO_2] = a_n e^{-kT},$$

wherein
- $n$ = said selected target kill level,
- $[ClO_2]$ = chlorine dioxide concentration of said treatment solution,
- $T$ = temperature of said treatment solution, and
- $a$, $k$ = empirically determined constants for a given kill level;

preheating water to a preheat temperature of at least about 20° C. in an auxiliary container;

mechanically breaking said container and said infectious waste in said auxiliary container into a particle size between about 0.4 to 1.5 cm for releasing and mixing said predetermined quantity of solid sodium chlorite salt and a predetermined quantity of solid citric acid with infectious waste particles in preheated water;

reacting said predetermined quantity of sodium chlorite salt and said predetermined quantity of solid citric acid in said preheated water to generate said treatment solution comprising chlorine dioxide and sodium citrate;

measuring an initial temperature and an initial chlorine dioxide concentration of said treatment solution;

comparing said initial temperature and said initial chlorine dioxide concentration to said curve;

adjusting the temperature of said treatment solution until said treatment solution achieves a temperature and a chlorine dioxide concentration on or above said curve to substantially disinfect said infectious waste.

13. The method for treating an infectious waste as recited in claim 12 further comprising adjusting the temperature of said treatment solution by adjusting said preheat temperature of said preheated water.

14. The method for treating an infectious waste as recited in claim 12 wherein the mechanically breaking and reacting steps are performed substantially simultaneously.

* * * * *